(12) United States Patent
Kogan et al.

(10) Patent No.: US 8,276,225 B2
(45) Date of Patent: *Oct. 2, 2012

(54) METHODS AND SYSTEMS FOR PATIENT POSITIONING IN AN IMAGING SYSTEM

(75) Inventors: Michael Kogan, Haifa (IL); Alexander Vaisburd, Haifa (IL); Danny Hausner, Haifa (IL); Yaron Hefetz, Herzeliya (IL)

(73) Assignee: General Electric Company, Schenectady, NY (US)

( * ) Notice: Subject to any disclaimer, the term of this patent is extended or adjusted under 35 U.S.C. 154(b) by 674 days.

This patent is subject to a terminal disclaimer.

(21) Appl. No.: 11/490,587

(22) Filed: Jul. 21, 2006

(65) Prior Publication Data

US 2007/0050908 A1    Mar. 8, 2007

Related U.S. Application Data

(60) Provisional application No. 60/710,528, filed on Aug. 23, 2005.

(51) Int. Cl.
*A47B 71/00* (2006.01)
*G21K 5/08* (2006.01)
*A61B 5/055* (2006.01)

(52) U.S. Cl. ............... 5/601; 378/68; 600/415; 600/425

(58) Field of Classification Search .................. None
See application file for complete search history.

(56) References Cited

U.S. PATENT DOCUMENTS

| | | |
|---|---|---|
| 3,652,851 A | 3/1972 | Zaalberg |
| 4,602,378 A | 7/1986 | Kelman et al. |
| 4,977,588 A | 12/1990 | Van der Ende |
| 5,029,826 A | 7/1991 | Schaefer |
| 5,078,142 A | 1/1992 | Siczek et al. |
| 5,613,254 A | 3/1997 | Clayman et al. |
| 5,950,262 A | 9/1999 | Smoler et al. |
| 6,194,725 B1 | 2/2001 | Colsher et al. |
| 6,237,172 B1 | 5/2001 | Morgan, Sr. |
| 6,298,506 B1 | 10/2001 | Heinold et al. |
| 6,357,066 B1 * | 3/2002 | Pierce ........................ 5/710 |
| 6,446,286 B1 * | 9/2002 | Karmalawy .................. 5/601 |
| 6,886,198 B2 | 5/2005 | Marin et al. |
| 6,899,459 B1 | 5/2005 | McKenna |

(Continued)

FOREIGN PATENT DOCUMENTS

WO    WO 2005/018735 A2    3/2005

(Continued)

OTHER PUBLICATIONS c.cam A Whole New Angle in Cardiology; Siemens Medical Solutions USA, Inc.; © 2005, Siemens AG, 16 pgs.

*Primary Examiner* — Tse Chen
*Assistant Examiner* — Angela M Hoffa
(74) *Attorney, Agent, or Firm* — The Small Patent Law Group; Dean D. Small

(57) ABSTRACT

Methods and systems for patient positioning in an imaging system are provided. A palette for an imaging system is provided that includes a base portion movably connected to the imaging system and an extender portion removably connected to the base portion. The extender portion together with the base portion supports an object to be imaged by the imaging system.

18 Claims, 10 Drawing Sheets

U.S. PATENT DOCUMENTS

| | | |
|---|---|---|
| 7,173,265 B2 | 2/2007 | Miller et al. |
| 7,242,002 B2 | 7/2007 | Blevis et al. |
| 7,288,759 B2 * | 10/2007 | Frangioni et al. ........... 250/252.1 |
| 7,540,661 B2 * | 6/2009 | Hornig ........................... 378/209 |
| 7,638,775 B2 * | 12/2009 | Kogan et al. ............. 250/370.09 |
| 2002/0032927 A1 | 3/2002 | Dinkler |
| 2004/0263865 A1 | 12/2004 | Pawlak et al. |
| 2005/0055773 A1 | 3/2005 | Cooke |
| 2005/0059877 A1 * | 3/2005 | Falbo, Sr. ....................... 600/407 |
| 2006/0002511 A1 | 1/2006 | Miller et al. |
| 2006/0186622 A1 | 8/2006 | Darling, III |
| 2007/0039101 A1 | 2/2007 | Luginbuhl et al. |
| 2007/0237305 A1 | 10/2007 | Youngblood-Johnson |

FOREIGN PATENT DOCUMENTS

WO    WO 2006/091239 A2    8/2006

* cited by examiner

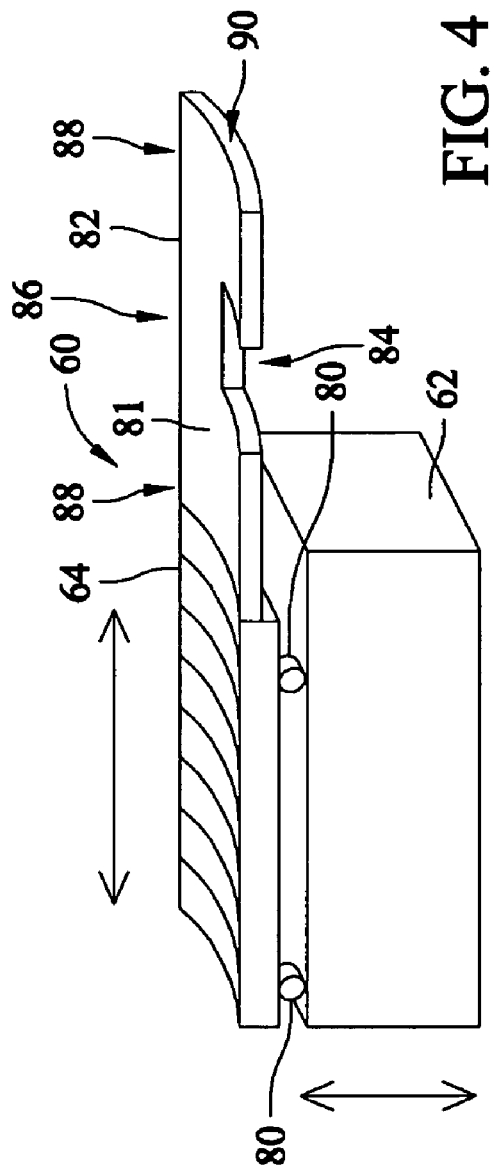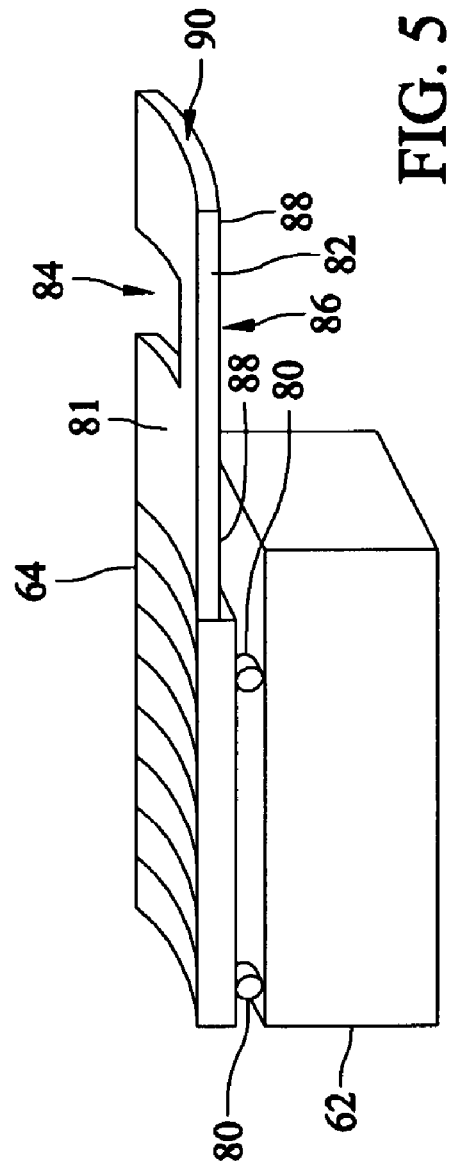

METHODS AND SYSTEMS FOR PATIENT POSITIONING IN AN IMAGING SYSTEM

CROSS REFERENCE TO RELATED APPLICATIONS

This application claims priority to and the benefit of the filing date of U.S. Provisional Application No. 60/710,528, filed on Aug. 23, 2005 and which is hereby incorporated by reference in its entirety.

BACKGROUND OF THE INVENTION

This invention relates generally to medical imaging systems and, more particularly, to a modular method of maintaining a stable patient position in medical imaging systems.

Medical imaging requires accurate and repeatable positioning of the patient for a scan and a table that facilitates minimizing attenuation of the gamma radiation. Attenuation of the gamma radiation increases the examination duration and affects negatively the image quality. Specifically, in a cardiac camera, low energy radiation is emitted and for which attenuation coefficients of structural members are higher, thereby aggravating the attenuation effects. During some scans a transmission measurement may also be acquired. Attenuation of the table may also negatively affect the transmission measurement. During a scan the patient heart may be located on a left-side or a right-side of the patient based on the patient position being supine or prone. Further, when imaging small children or babies makeshift means are used to hold and to restrain the child or baby. Often full sedation is required and adhesive tapes may be used. Additionally, calibration sources and phantoms are typically manually positioned on the patient table when conducting calibrations and testing, which can lead to improper alignment resulting in reduced image resolution.

Thus, known systems and methods to maintain a stable patient position often may not be accurate and repeatable. Further, image resolution may be affected and duration of exposure to radiation may be increased, resulting in increased potential risk to a patient.

BRIEF DESCRIPTION OF THE INVENTION

In one embodiment, a palette for an imaging system is provided that includes a base portion movably connected to the imaging system and an extender portion removably connected to the base portion. The extender portion together with the base portion supports an object to be imaged by the imaging system.

In another embodiment, a modular support system for a medical imaging system is provided that includes a modular palette configured to be changed based on a type of scan to be performed by the medical imaging system and a connection member configured to removably connect the modular palette to the medical imaging system.

In yet another embodiment, a method for medical imaging using a modular table palette is provided. The method includes configuring the modular table palette to be removably connected to a table of a medical imaging system and supporting at least a portion of patient to be imaged on the modular table palette removably connected to the table.

BRIEF DESCRIPTION OF THE DRAWINGS

FIG. 4 is perspective view of an exemplary modular palette constructed in accordance with another embodiment of the invention and configured for cardiac scans.

FIG. 5 is another perspective view of the modular palette shown in FIG. 4 in which the orientation of the modular palette is reversed.

DETAILED DESCRIPTION OF THE INVENTION

As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

Figure 1:
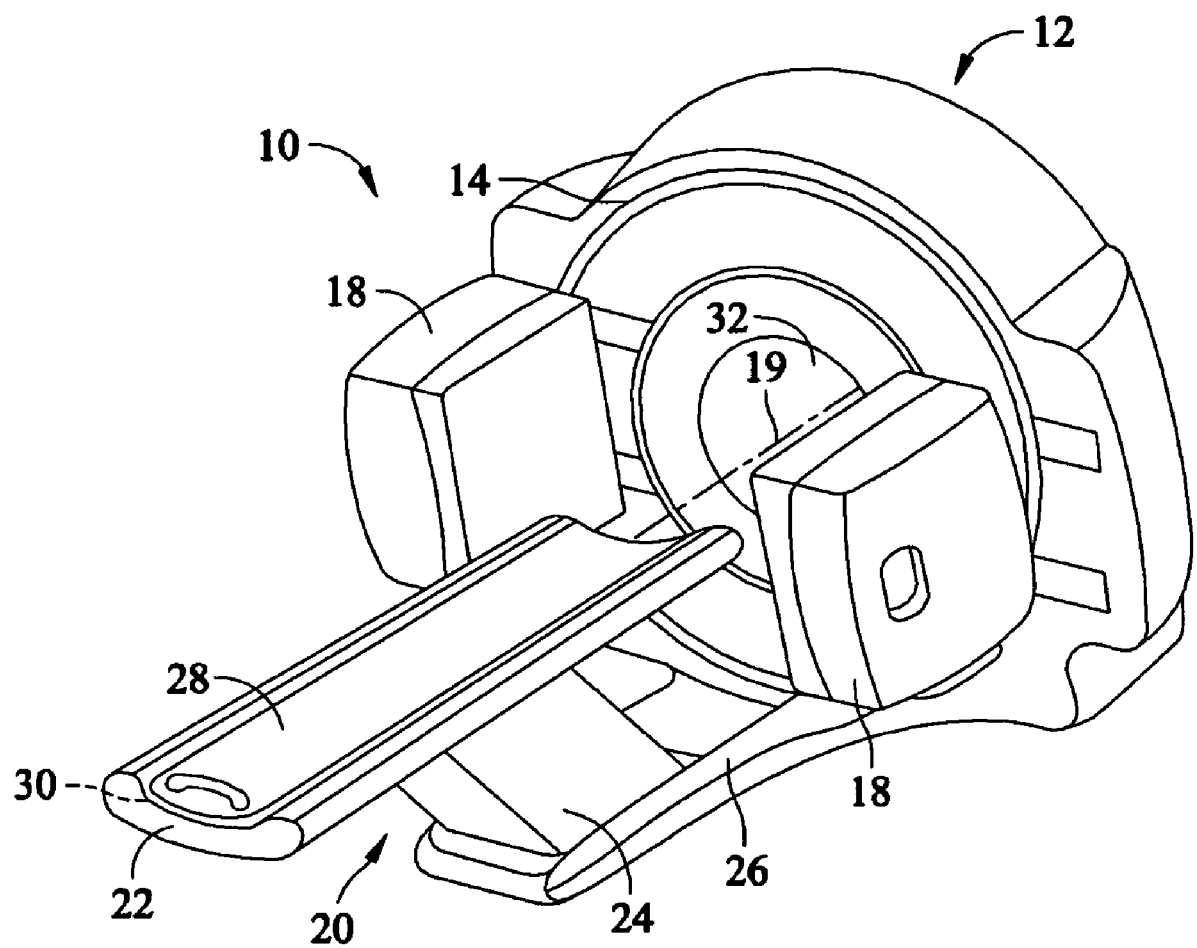
FIG. 1 is a perspective view of an exemplary nuclear medicine imaging system constructed in accordance with an embodiment of the invention.

FIG. 1 is a perspective view of an exemplary embodiment of a medical imaging system 10 constructed in accordance with various embodiments of the invention, which in this embodiment is a nuclear medicine imaging system. The system 10 includes an integrated gantry 12 that further includes a rotor 14 oriented about a gantry central bore 17. The rotor 14 is configured to support one or more nuclear medicine (NM) cameras 18, such as, but not limited to gamma cameras, SPECT detectors, and/or PET detectors. The rotors 14 is further configured to rotate axially about an examination axis 19. A patient table 20 may include a bed 22 slidingly coupled to a bed support system 24, which may be coupled directly to a floor or may be coupled to the gantry 12 through a base 26 coupled to gantry 12. The bed 22 may include a stretcher 28 slidingly coupled to an upper surface 30 of the bed 22. The patient table 20 is configured to facilitate ingress and egress of a patient (not shown) into an examination position that is substantially aligned with examination axis 19. During an imaging scan, the patient table 20 may be controlled to move the bed 22 and/or stretcher 28 axially into and out of a bore 32. The operation and control of the imaging system 10 may be performed in any known manner.

Figure 2:
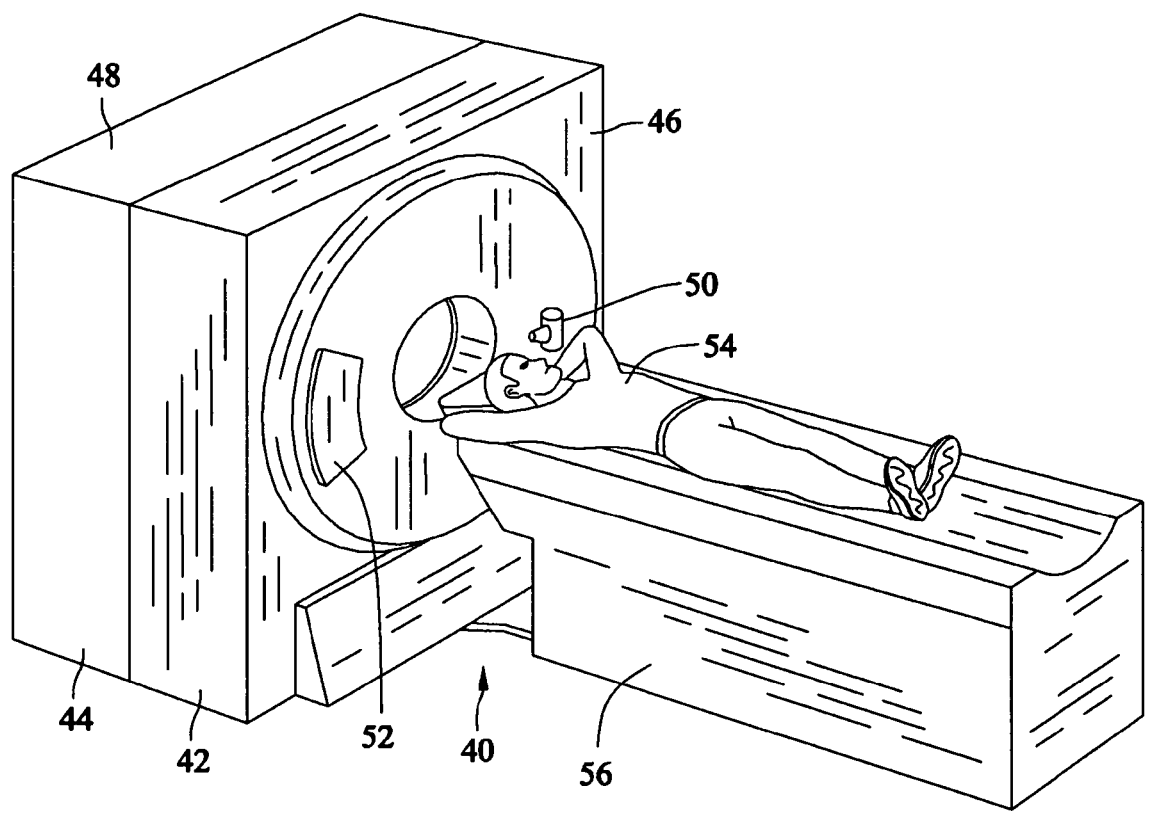
FIG. 2 is a perspective view of an exemplary multi-modal imaging system constructed in accordance with an embodiment of the invention.

FIG. 2 is a perspective view of an exemplary imaging system 40 constructed in accordance with various embodiments of the invention, which in this embodiment is a multi-modal imaging system. In the exemplary embodiment, the imaging system 10 includes a first modality unit 42 and a second modality unit 44. The modality units 42 and 44 enable the system 40 to scan an object, for example, a patient, in a first modality using the first modality unit 42 and to scan the object in a second modality using the second modality unit 44. The system 40 allows for multiple scans in different modalities to facilitate an increased diagnostic capability over single modality systems. In one embodiment, the multi-modal imaging system 40 is a Computed Tomography/Positron Emission Tomography (CT/PET) imaging system 40. The CT/PET system 40 includes a first gantry 46 associated with the first modality unit 42 and a second gantry 48 associated with the second modality unit 44. In alternative embodiments, modalities other than CT and PET may be employed with the imaging system 40 The gantry 46, in an embodiment, includes the first modality unit 42 that has an x-ray source 50 that projects a beam of x-rays (not shown) toward a detector array 52 on the opposite side of the gantry 46. The detector array 52 is formed by a plurality of detector rows (not shown) including a plurality of detector elements (not shown) that together sense the projected x-rays that pass through an object, such as a patient 54 that may be supported on a table 56. Each detector element produces an electrical signal that represents the intensity of an impinging x-ray beam and allows estimation of the attenuation of the beam as the beam passes through the object or patient 54.

In other embodiments, the system 40 includes only a single gantry having a first rotor configured to carry the first modality system and a second rotor configured to carry the second modality system. In various other embodiments the system 40 includes only one modality, such as NM (as shown in FIG. 1) or CT.

In general, during a scan to acquire data using either the imaging system 10 or 40, the gantry 12 or 46, 48 and/or components mounted thereon, such as the rotor, rotate about an examination axis, for example, the examination axis 19. The rotation the operation of the detectors or energy sources may be controlled by any known control mechanism of the system 10 or 40. During the scan, image data is acquired in any known manner, which then may be processed (e.g., reconstructed) to form one or more images of the object, such as the patient 54.

Additionally, although described in a medical setting, it is contemplated that the embodiments of the invention may be implemented in connection with other imaging systems including industrial CT systems such as, for example, but not limited to, a baggage scanning CT system typically used in a transportation center such as, for example, but not limited to, an airport or a rail station, non-destructive testing systems, etc.

Figure 3:
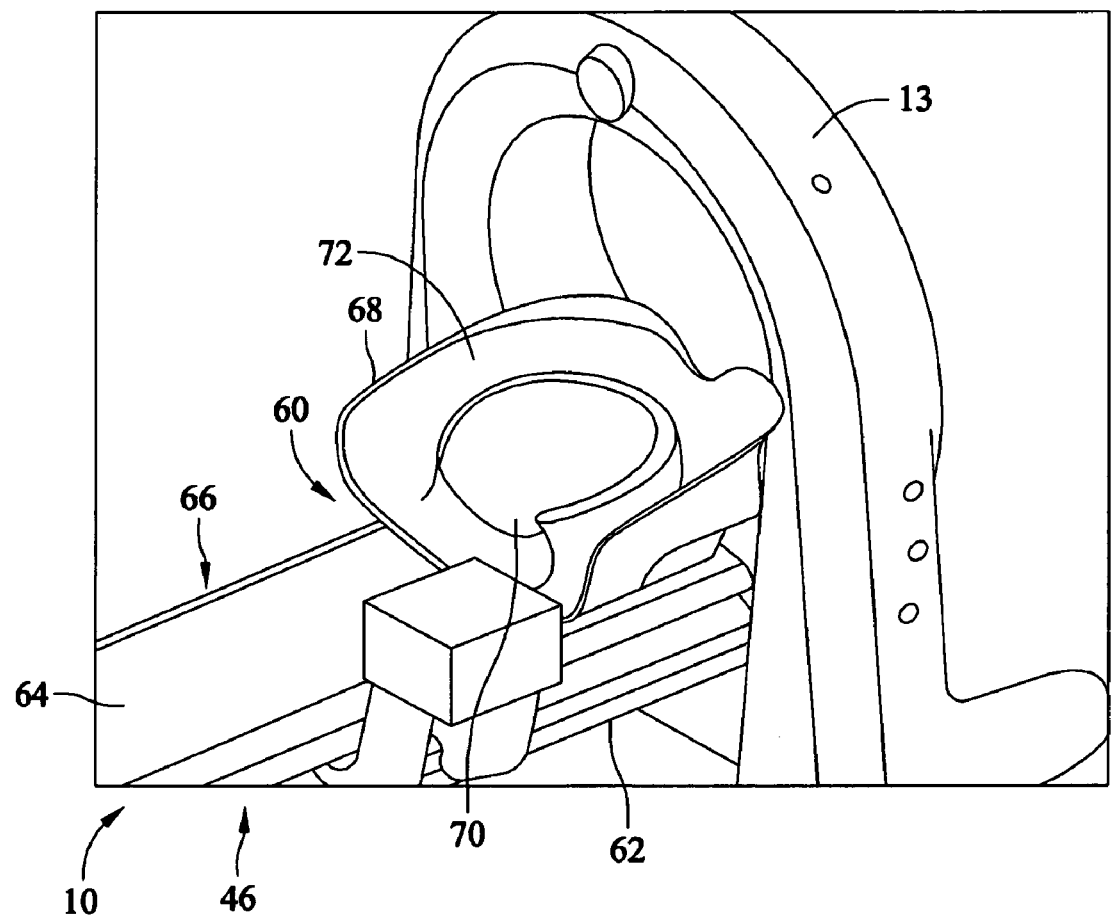
FIG. 3 is a perspective view of an exemplary modular palette constructed in accordance with an embodiment of the invention and configured for general applications.

FIG. 3 is a perspective view of an exemplary modular palette 60 configured for general applications, for example, configured to maintain the position of a patient 22 (shown in FIG. 1) during different types of imaging scans or examinations. The modular palette 60 is removably connected to the imaging system 10, and more particularly, to the motorized table 46 of the imaging system 10. The motorized table 46 includes a stationary table frame 62 and a movable table portion 64. In this embodiment, the gantry is a single gantry, for example, the gantry 13 with a plurality of detector elements (not shown). The modular palette 60 is removably connected to a top portion 66 of the movable table portion 64, for example, within a slot or depression (not shown) within the movable table portion 64. The movable table portion 64 is supported on the stationary table frame 62 and may include movable members 80 (shown in FIG. 4) configured to allow movement of the movable table portion 64, for example, laterally in and out of the gantry 13 (shown in FIG. 3). It should be noted that the stationary table frame 62 also may be configured to provide upward and downward movement of the movable table portion 64.

The modular palette 60 optionally may include a head/arm rest 68 coupled to an end of the modular palette 60, for example, removably connected (e.g., snap fit) in any known manner. The head/arm rest 68 generally includes an inner depression 70 or recessed portion for receiving therein a head (e.g., back portion of a head) of the patient 22 and an outer depression 72 or recessed portion. The outer recessed portion 72 is configured, for example, to maintain the position of the arms of a patient 22 around and above the head of the patient 22. In an alternative embodiment, the head/arm rest 68 is removably coupled to a top surface of the modular palette 60. The modular palette 60 and the head/arm rest 68 may be constructed of any material, for example, a hard plastic with a foam or cushioned cover that contacts a patient 22 supported thereon.

FIG. 4 is perspective view of the modular palette 60 configured for cardiac scans. The modular palette 60 is removably connected to the movable table portion 64, for example, within a slot or depression (not shown) within a front edge of the movable table portion 64. The movable table portion 64 is supported on the stationary table frame 62 and may include the movable members 80 (e.g., wheels) configured to allow movement of the movable table portion 64, for example, laterally in and out of the gantry 13 (shown in FIG. 3). The stationary table frame 62 also may be configured to provided upward and downward movement of the movable table portion 64.

The modular palette 60 palette provides "zero" table attenuation for a supine position. In this embodiment, the modular palette 60 is configured as a table stretcher that generally include a base portion 81 defined by the movable table portion 64 and an extender portion 82. The extender portion 82 includes a lateral notch 84, making the extender portion 82 axially asymmetrical in, for example, a patient heart area. A mechanical interface (not shown) may be provided in any known manner and that connects the extender portion 82 to the base portion 81. The mechanical interface is substantially identical in a supine position and in a prone position such that the extender portion 82 may be coupled to the base portion 81 using either end of the extender portion 82 or when the extender portion 82 is inverted. In these various connection orientations the notch 84 is oriented either on a left side or a right side of the movable table portion 64, for example, based on the patient position (e.g., prone or supine position). Also, the notch 84 may be located generally at a middle portion 86 of the extender portion 82 of at one of an end portion 88 of the extender portion 82.

In operation, in each position of the notch 82, the axial dimension of the extender portion 82 ensures that the location of the patient heart is in the middle of the notch 82 while the patient head is located next to an outer side 90, for example, at an end 88 of the extender portion 82. The depth of the notch 82 may be provided such that in all positions of detectors during a scan (e.g., up to 180 degrees in cardiac cameras) the gamma rays, emitting from the heart area, are received by the detectors while avoiding attenuation in the material of the extender portion 82.

FIG. 5 is a perspective view of the modular palette 60 in a different orientation than that shown in FIG. 4. In particular, the extender portion 82 is configured for a patient lying in the prone position during a cardiac scan. In this embodiment, the extender portion 82 is coupled to the base portion 81 using an opposite end of the extender portion 82 or in an inverted (i.e., upside down) position such that the notch 84 is located proximate the patient heart (e.g., on the left side of the movable table portion 64) with the patient 26 (shown in FIG. 1) in the prone position. The notch 84 provides, for example, a cardiac gamma camera with "zero" table attenuation for a patient in the prone position.

Figure 6:
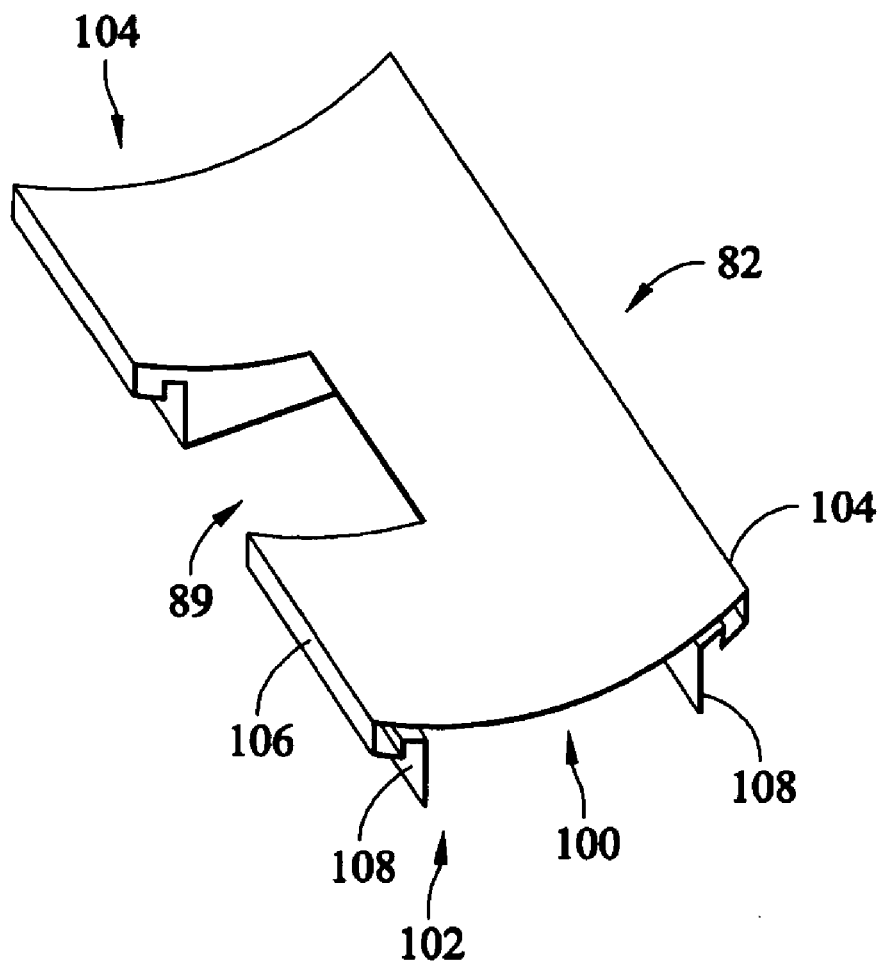
FIG. 6 is a perspective of view of an exemplary extender constructed in accordance with an embodiment of the invention and that may be used during cardiac scans.
Figure 7:
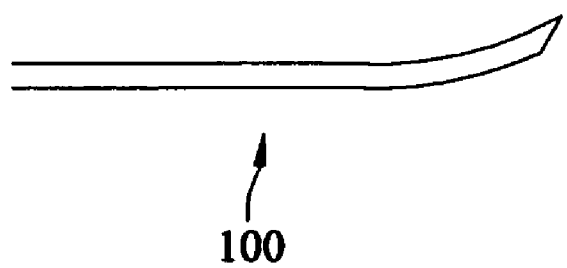
FIG. 7 is a side elevation view of the extender shown in FIG. 6.
Figure 8:
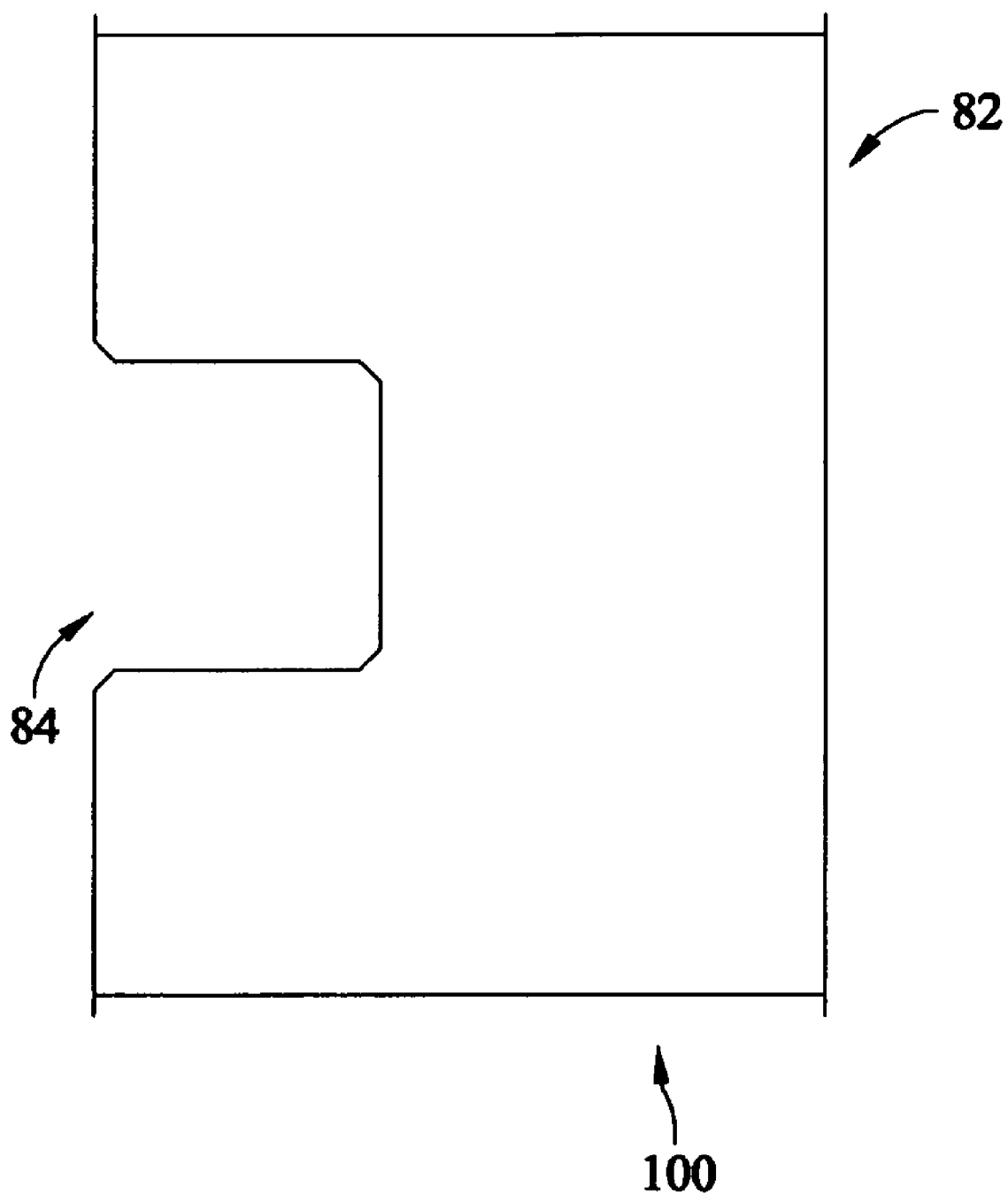
FIG. 8 is a top plan view of the extender shown in FIG. 6.

FIG. 6 is a perspective of view of an exemplary embodiment of the extender portion 82. The extender portion 82 generally includes an arcuate body 100 extending between a first coupling end 102 and a second coupling end 104. The body 100 also includes two parallel edges 106 extending between the first coupling end 102 and the second coupling end 104. At least one of the edges 106 includes the notch 84, configured as a substantially rectangular notch extending inward from the one edge 106. Each of coupling ends 100 and 104 are configured to mate to a complimentary coupling end of the base portion 81, for example, to an end of the movable table portion 64. For example, downward extending projections 108 may define feet or legs of the extender portion 82. The downward extending projections 108 in the various embodiments are configured to maintain the position of the extender portion 82 to the movable table portion 64 and/or the connection of the extender portion 82 to the movable table portion 64. FIGS. 7 and 8 show a side elevation view and top plan view of the extender portion 82, respectively.

Figure 9:
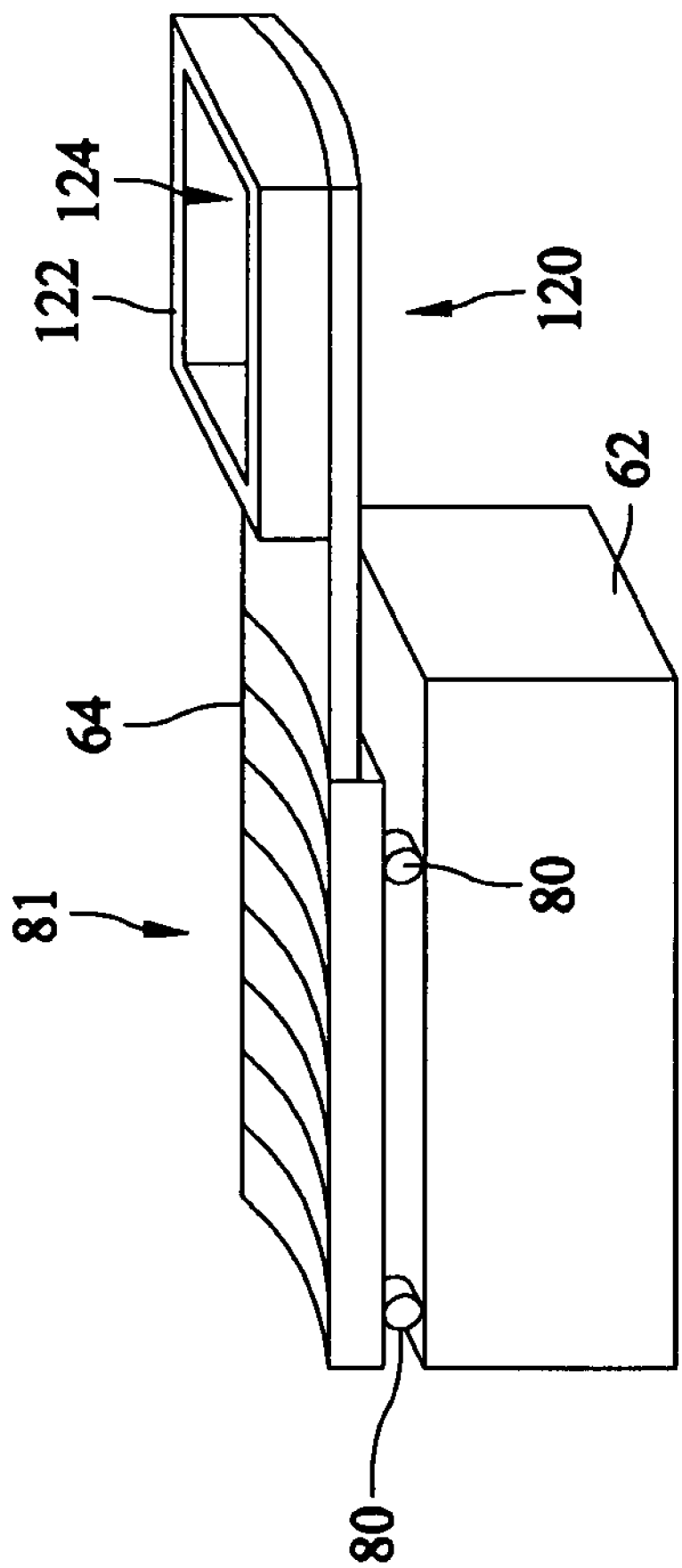
FIG. 9 is a perspective view of an exemplary extender constructed in accordance with another embodiment of the invention that may be used during a pediatric scan.

FIG. 9 is a perspective view of another exemplary extender portion 120 that is configured to be used, for example, for a pediatric patient. The extender portion 120 includes a cradle portion 122 that includes a depression 124 that may be sized to accommodate a pediatric patient. Different sizes of depressions 124 may be provided, for example, for use on different sizes of babies or infants. The extender portion 120 permits positioning the pediatric patient such that, for example, a detector radius used to image a pediatric patient is less than the detector radius used to scan an adult patient. Further, the cradle portion 122 is configured to be replaced with other cradle portions 122 of various sizes to accommodate various sizes of pediatric patients, for example, by removable connection. The extender portion 120 may be removably connected to the base portion 81, for example, to an end of the movable table portion 64 in any known manner and/or in a complimentary connection arrangement as described herein. It should be noted that image quality of a nuclear camera operating in a Single Photon Emission Computed Tomography (SPECT) mode degrades with an increase in the rotation radius of the nuclear camera around the patient. Using a small pediatric cradle, such as the cradle portion 122, allows a smaller rotation radius and thus increased resolution and image quality.

Figure 10:
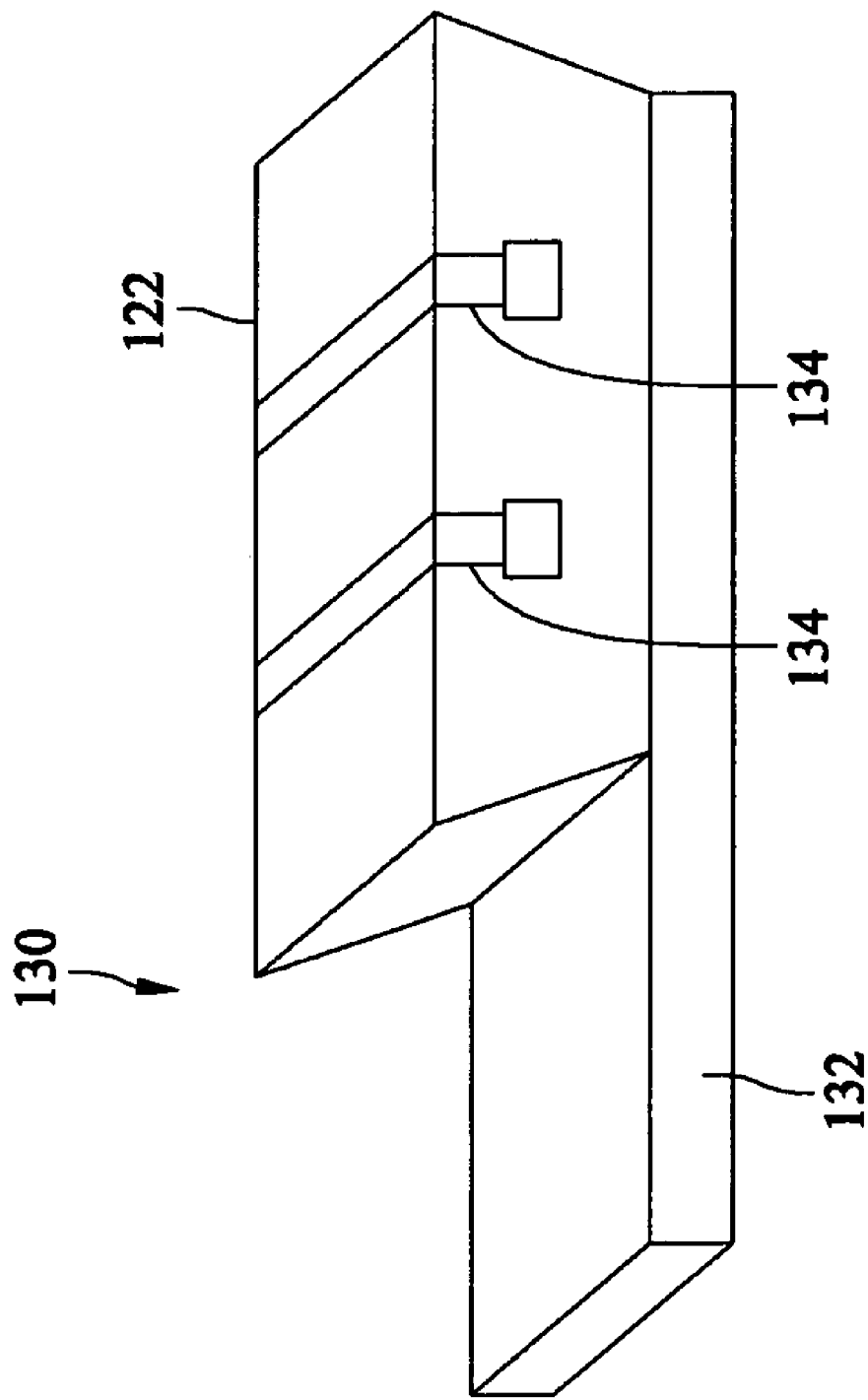
FIG. 10 is a perspective view of an exemplary extender constructed in accordance with another embodiment of the invention that may be used during a pediatric scan.

FIG. 10 is a perspective view of another exemplary extender portion 130 that also is configured to be used, for example, for a pediatric patient. In this exemplary embodiment, the extender portion 130 includes a substantially planar surface 132 generally defining a base and includes optional restraints 134 (e.g., straps) configured to facilitate maintaining the pediatric patient on the cradle portion 122. In an alternative embodiment, the extender portion 130 includes the cradle portion 122 with the depression 124 (shown in FIG. 9). The optional restraints further facilitate maintaining the pediatric patient positioned on the extender.

Figure 11:
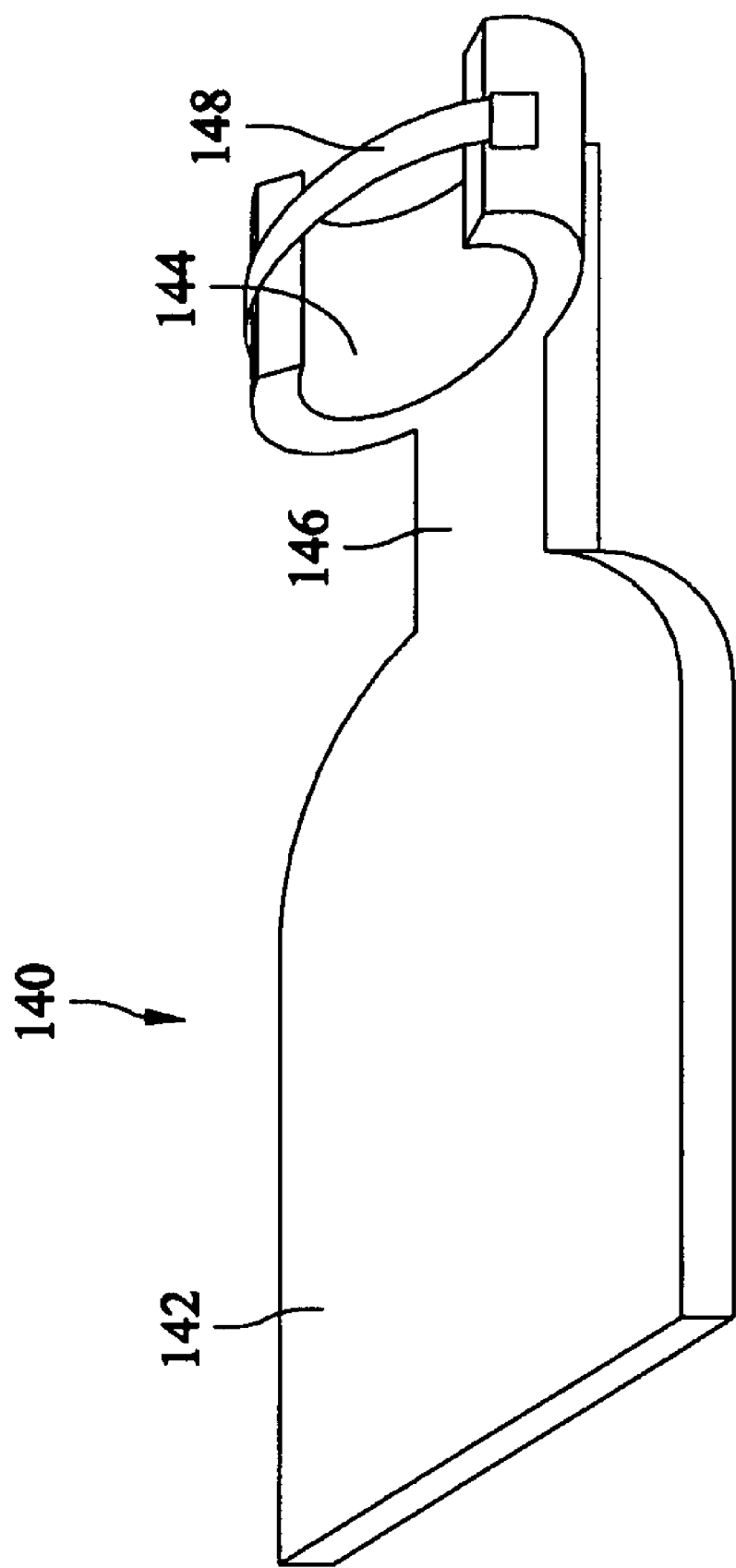
FIG. 11 is a perspective view of an exemplary modular extender constructed in accordance with another embodiment of the invention that may be used during a cranial scan.

FIG. 11 is a perspective view of another exemplary extender portion 140 that is configured, for example, for a cranial examination of a patient. The extender portion 140 includes a base portion 142 that may support the upper back portion of a patient and a headrest portion 144 configured to support the head of the patient. The headrest portion 144 may be provided on an extension portion 146 that also is configured to support the neck of the patient and has a smaller width than the portion to support the upper back of the patient. The headrest portion 144 is configured as an arcuate headrest that includes an optional restraint 148 (e.g., strap) configured to immobilize the patient head. It should again be noted that the image quality of a nuclear camera operating in a SPECT mode degrades with an increase in the rotation radius of the nuclear camera around the patient. Using a narrow headrest, such as the headrest portion 144 allows a smaller rotation radius and thus increased resolution and image quality.

Figure 12:
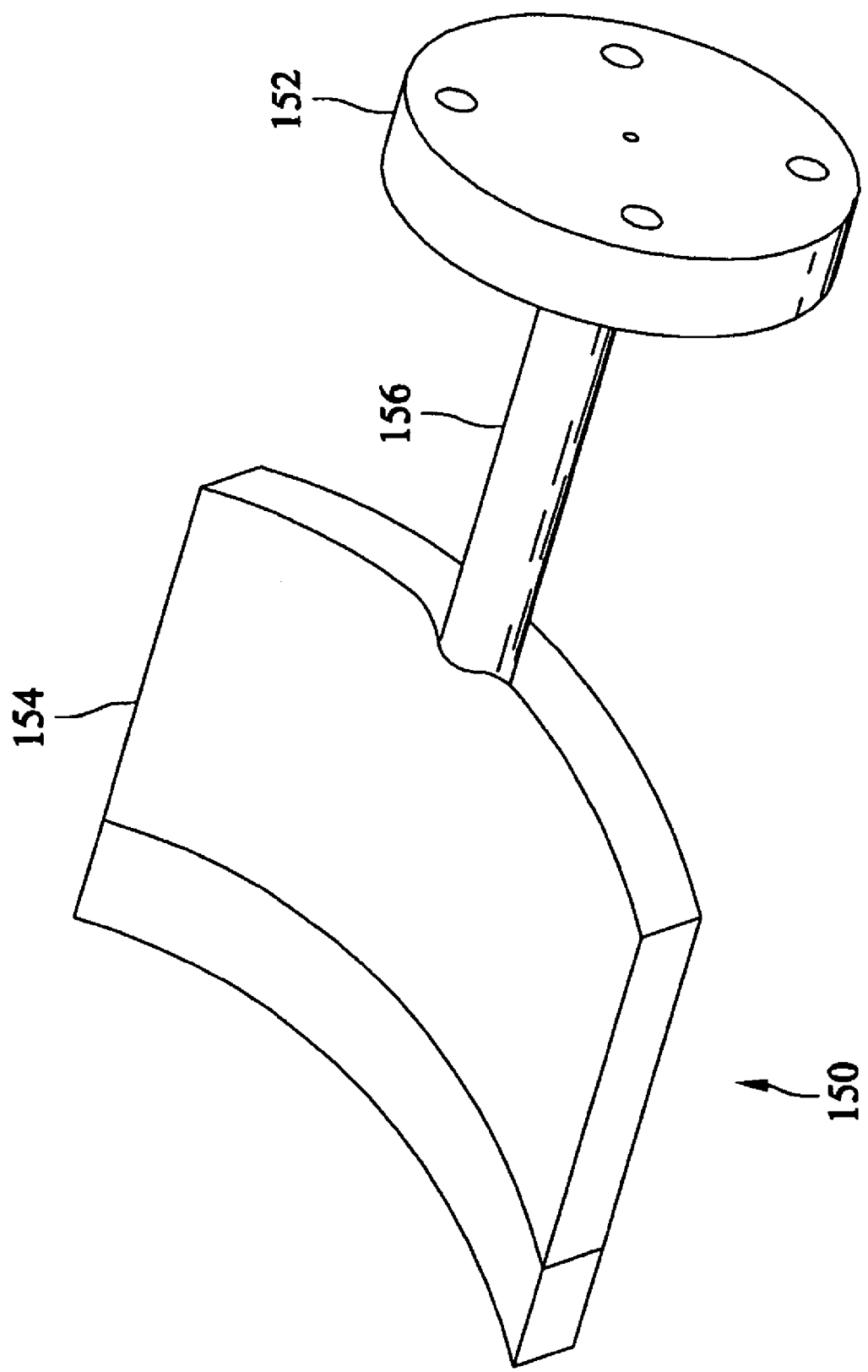
FIG. 12 is a perspective view of an exemplary extender constructed in accordance with another embodiment of the invention configured to support calibration sources and phantoms.

FIG. 12 is a perspective view of another exemplary extender portion 150 configured to support a calibration source 152 and/or phantom that are provided in any known manner. The extender portion 150 includes a base 154 that includes a coupling configured to couple the base 154 to the movable table portion 64 (shown in FIGS. 4, 5, and 9) as described herein or in an known manner. The extender portion 150 includes a substantially cylindrical extension 156 configured to support the calibration source 152 and/or phantom, for example, a cylindrical source drum provided in any known manner. It should again be noted that the image quality of a nuclear camera operating in a SPECT mode degrades with an increase in the rotation radius of the nuclear camera around the patient. Using a narrow phantom attachment, such as provided by the extender portion 150 allows a smaller rotation radius and thus increased resolution and image quality.

It should to be noted that the extender portions may be modified or different extender portions provided to support a patient or a portion of a patient for different examinations, scans or applications. Also, the connection or engagement portion for removably connecting or engaging the extender portion to the imaging system may be provided in any known manner, such as snap fit, compression fit, etc.

Although various embodiments are described above relative to a particular imaging system, for example a nuclear medicine system, other medical imaging modalities, such as computed tomography (CT), single positron emission tomography (SPECT), positron emission tomography (PET), nuclear magnetic resonance imaging (MRI), static X-ray imaging, dynamic (Fluoroscopy) X-ray imaging, and multi-modality combinations thereof may also benefit form the methods described herein and the use of the various embodiments of the present invention is contemplated with respect to these modalities. Also, the various embodiments may be used in connection with non-medical imaging systems.

The above-described embodiments of a medical imaging system provide a cost-effective and reliable means for using a plurality of interchangeable modular extensions for a patient table base. The extensions are configured to provide ergonomic and comfort features to, for example, ease the anxiety of patients and expedite scanning by technicians.

Exemplary embodiments of medical imaging systems and methods are described above in detail. The medical imaging system components illustrated are not limited to the specific embodiments described herein, but rather, components of each system may be utilized independently and separately from other components described herein. For example, the medical imaging system components described above may also be used in combination with different medical imaging system components. Further, the removable sections or portions of the palette may be removed and reattached by a single user, which in the various embodiments, may be performed without a mechanical tool.

A technical effect of the various embodiments of the systems and methods described herein include facilitating operation of a medical imaging system by providing patient support and comfort that is compatible with zero attenuation of the camera radiation during a scan. For example, an extender provides a notch in the heart area of the patient regardless of the patient's supine or prone position. The notch provides zero table attenuation.

While the invention has been described in terms of various specific embodiments, those skilled in the art will recognize that the various embodiments of the invention can be practiced with modification within the spirit and scope of the claims.

What is claimed is:

1. A palette for a medical imaging system configured to support a patient thereon, said palette comprising:
 a base portion configured to couple to a table, the table configured to move along an examination axis into a bore of an imaging system, the base portion having a base support surface that extends along the examination axis; and
 a modular extender portion configured to removably couple to the base portion, the extender portion comprising:
  a lateral notch formed in the extender portion, the lateral notch configured to be inserted into the bore of the imaging system to enable gamma rays emitted from a source to be transmitted through the notch and received at a detector, wherein the lateral notch is configured to connect to the base portion such that the lateral notch is positioned toward a first side and is also configured to connect to the base portion such that the lateral notch is positioned toward a second side of the base portion while the table is maintained in the same operational position;
  first and second edges that extend parallel to the examination axis;
   a support section that extends laterally between and joins the first and second edges, the support section having a modular support surface that extends along the examination axis, wherein the base and modular support surfaces are configured to support thereon different portions of the patient;
   first and second coupling ends, the support section and the first and second edges extending between the first and second coupling ends along the examination axis, the first and second coupling ends being configured to, separately, removably couple to the base portion; and
   first and second leg projections coupled to the first and second edges, respectively, and extending longitudinally along the examination axis between the first and second coupling ends, each of the first and second leg projections extending downward away from the support section and being located inward from the respective first and second edges such that a lateral distance between an outer edge of the first and second leg projections is less than a lateral distance between the first and second edges.

2. A palette in accordance with claim 1 wherein the first and second leg projections are shaped to directly engage corresponding slots of the table to removably couple the extender and base portions to the table.

3. A palette in accordance with claim 1 wherein each of the first and second edges extends downward away from the support section, each of the first and second edges also extending inward to a corresponding leg projection, and wherein the support section, the first and second edges, and the first and second leg projections are shaped from a continuous sheet of material having a substantially uniform thickness throughout.

4. A palette in accordance with claim 3 wherein the continuous sheet of material is shaped so that the modular support surface has an arcuate contour that curves about the examination axis.

5. A palette in accordance with claim 1 wherein the base and modular support surfaces join each other at an interface when the extender portion is removably coupled to the base portion at the first coupling end or at the second coupling end, the base and modular support surfaces collectively forming a substantially continuous table surface that extends through the interface along the examination axis.

6. A palette in accordance with claim 1 wherein each of the first and second coupling ends is shaped to snap-fit to the base portion.

7. A support system configured to support a patient in a medical imaging system, the support system comprising:
 a base portion configured to couple to a table, the table configured to move along an examination axis into a bore of an imaging system, the base portion having a base support surface that extends along the examination axis;
 a modular extender portion configured to removably couple to the base portion, the extender portion comprising:
  first and second edges that extend parallel to the examination axis;
  a support section that extends laterally between and joins the first and second edges, the support section having a modular support surface that extends along the examination axis, wherein the base and modular support surfaces are configured to support thereon different portions of the patient;
  first and second coupling ends, the support section and the first and second edges extending between the first and second coupling ends along the examination axis, the first and second coupling ends being configured to, separately, removably couple to the base portion;
  first and second leg projections coupled to the first and second edges, respectively, and extending longitudinally along the examination axis between the first and second coupling ends, each of the first and second leg projections extending downward away from the support section and being located inward from the respective first and second edges such that a lateral distance between the first and second leg projections is less than a lateral distance between the first and second edges; and
 a substantially cylindrical extension coupled to the extender portion, the cylindrical extension having a first end coupled to the extender portion and a second end configured to receive either a phantom or calibration source thereon; and
 a table frame supporting the base portion, the base and extender portions being movable in a direction along the examination axis with respect to the table frame.

8. A support system in accordance with claim 7 wherein the table frame directly supports both the base and extender portions such that the table frame contacts both the base and extender portions.

9. A support system in accordance with claim 7 wherein the support section, the first and second edges, and the first and second leg projections are shaped from a continuous sheet of material.

10. A support system in accordance with claim 7 wherein each of the first and second coupling ends is shaped to snap-fit to the base portion.

11. A support system in accordance with claim 7 wherein the first and second leg projections are shaped to directly engage and be inserted into corresponding slots of the base portion or the table frame to removably couple the extender and base portions.

12. A support system in accordance with claim 7 wherein the extender portion is a general-purpose extender portion and the modular support surface is substantially continuous between the first and second edges and the first and second coupling ends, the system further comprising a plurality of secondary extender portions configured for different types of imaging scans, each of the secondary extender portions having a corresponding coupling end that is substantially identical to the first and second coupling ends of the general-purpose extender portion and each of the secondary extender portions having a corresponding support surface that is configured for a different type of imaging scan.

13. A support system in accordance with claim 7 wherein each of the first and second edges extends downward away from the support section, each of the first and second edges also extending inward to the corresponding leg projection.

14. A support system in accordance with claim 7 wherein the extender portion further comprises:
an extender base portion to support an upper back of the patient; and
a headrest portion configured to support the head of the patient, the headrest portion being separated from the extender base portion by an extension portion.

15. A support system in accordance with claim 14 wherein the headrest portion includes a restraint configured to immobilize the patient's head.

16. A palette for a medical imaging system configured to support a patient thereon, said palette comprising:
a base portion configured to be coupled to a table, the table configured to move along an examination axis into a bore of an imaging system, the base portion having a base support surface that extends along the examination axis; and
a modular extender portion configured to removably couple to the base portion, the extender portion comprising a cradle portion coupled to the extender portion, the cradle portion adapted to receive a pediatric patient therein, the extender portion further comprising a lateral notch formed in the extender portion, the lateral notch configured to be inserted into the bore of the imaging system to gamma rays emitted from a source to be transmitted through the notch and received at a detector, wherein the lateral notch is configured to connect to the base portion such that the lateral notch is positioned toward a first side and is also configured to connect to the base portion such that the lateral notch is positioned toward a second side of the base portion while the table is maintained in the same operational position.

17. A palette in accordance with claim 16, wherein the cradle portion includes a plurality of walls forming an enclosed depression, the enclosed depression adapted to receive the pediatric patient therein.

18. A palette in accordance with claim 16, wherein the cradle portion includes a plurality of restraints adapted to maintain the pediatric patient within the cradle portion.

* * * * *